United States Patent [19]
Kolpak

[11] Patent Number: 5,237,852
[45] Date of Patent: Aug. 24, 1993

[54] MEASUREMENT OF GAS PROPERTIES

[75] Inventor: Miroslav M. Kolpak, Plano, Tex.

[73] Assignee: Atlantic Richfield Company, Los Angeles, Calif.

[21] Appl. No.: 855,954

[22] Filed: Mar. 23, 1992

[51] Int. Cl.$^5$ ............................................. G01N 33/00
[52] U.S. Cl. .................................................. 73/23.2
[58] Field of Search .............................. 73/23.2, 149

[56] References Cited

U.S. PATENT DOCUMENTS

| | | | |
|---|---|---|---|
| 3,701,280 | 10/1972 | Stroman | 73/23.2 X |
| 4,781,061 | 11/1988 | Baumgartl | 73/149 |
| 5,001,924 | 3/1991 | Walter et al. | 73/149 |

FOREIGN PATENT DOCUMENTS

| | | | |
|---|---|---|---|
| 1362938 | 12/1987 | U.S.S.R. | 73/23.2 |
| 8806291 | 8/1988 | World Int. Prop. O. | 73/23.2 |

Primary Examiner—Hezron E. Williams
Assistant Examiner—Joseph W. Roskos
Attorney, Agent, or Firm—Michael E. Martin

[57] ABSTRACT

Systems for determining the gas compression exponent, k, and the compressibility factor, Z, include a chamber which may be reduced in volume while the pressure, temperature and volume changes are recorded. The system for determining compressibility factor includes a temperature controller and heat exchanger which varies the temperature in the chamber after a compression process or while holding the volume of the chamber constant during multiple temperature changes. Values of pressure, temperature and volume are measured at all conditions. The compression exponent is measured by extrapolating a curve of pressure versus time while allowing the temperature of the gas to decay from heat exchange with the structure forming the chamber. The compressibility factor is determined by comparing the ratios of compressibility factors at three separate conditions of pressure, volume and temperature using an iterative technique based on an equation which utilizes a curve fitted form of the Standing Katz diagram having variables which include a pseudo-reduced temperature.

19 Claims, 5 Drawing Sheets

MEASUREMENT OF GAS PROPERTIES

BACKGROUND OF THE INVENTION

1. Field of the Invention

The present invention pertains to methods and systems for measuring the polytropic or isentropic compression exponent, the compressibility factor, the molecular weight and the pseudo-critical pressure and temperature for gases.

2. Background

In gas compression and process operations it is important to know the properties of gases such as the so-called polytropic compression exponent and, particularly, the isentropic exponent, the compressibility factor and the molecular weight of the gas or gas mixture. These properties are widely used in gas compression and transport applications for adjusting compressor operating characteristics, defining the heating value of gases, for example, and determining the amount of gas handled in transport and custody transfer applications.

Although these properties can be determined by laboratory analysis of samples of the gas in question, such processes are time-consuming and the properties of the gas may change between the time of sampling and obtaining measurement results. Accordingly, it has become increasingly evident that a type of "on-line" measurement method and system for determining the above-mentioned gas properties is particularly important. The present invention provides unique methods and systems for determining these gas properties in the so-called on-line manner.

SUMMARY OF THE INVENTION

The present invention provides a unique method for determining the polytropic or isentropic exponent associated with gas compression processes. The present invention also provides unique methods for determining the compressibility factor and molecular weight of gases in a rapid manner so that changes in gas composition may be readily accounted for.

The present invention further provides a unique system for determining the gas compression exponent (polytropic or isentropic) which is particularly adapted for making so-called on-line measurements of this gas property in a manner which is faster and better adapted for changes in the gas composition than previous systems.

The present invention still further provides a system for determining the compressibility factor of a gas and, in particular, in a so-called on-line manner whereby the compressibility factor is more rapidly and continuously determined so as to be of benefit to gas transport and handling processes.

The unique methods and systems in accordance with the present invention eliminate cost and time delays associated with sampling gas and removing the gas samples for laboratory analysis and provides for measuring gas properties even with rapid changes in gas composition associated with the production of certain gases, such as natural gas, for example.

The above-noted advantages of the present invention, together with other superior features and aspects thereof will be further appreciated by those skilled in the art upon reading the detailed description which follows in conjunction with the drawing.

DESCRIPTION OF PREFERRED EMBODIMENTS

In the description which follows, like parts are marked throughout the specification and drawing with the same reference numerals, respectively. Certain of the drawing figures are schematic diagrams showing elements in rather generalized form in the interest of clarity and conciseness.

Figure 1:
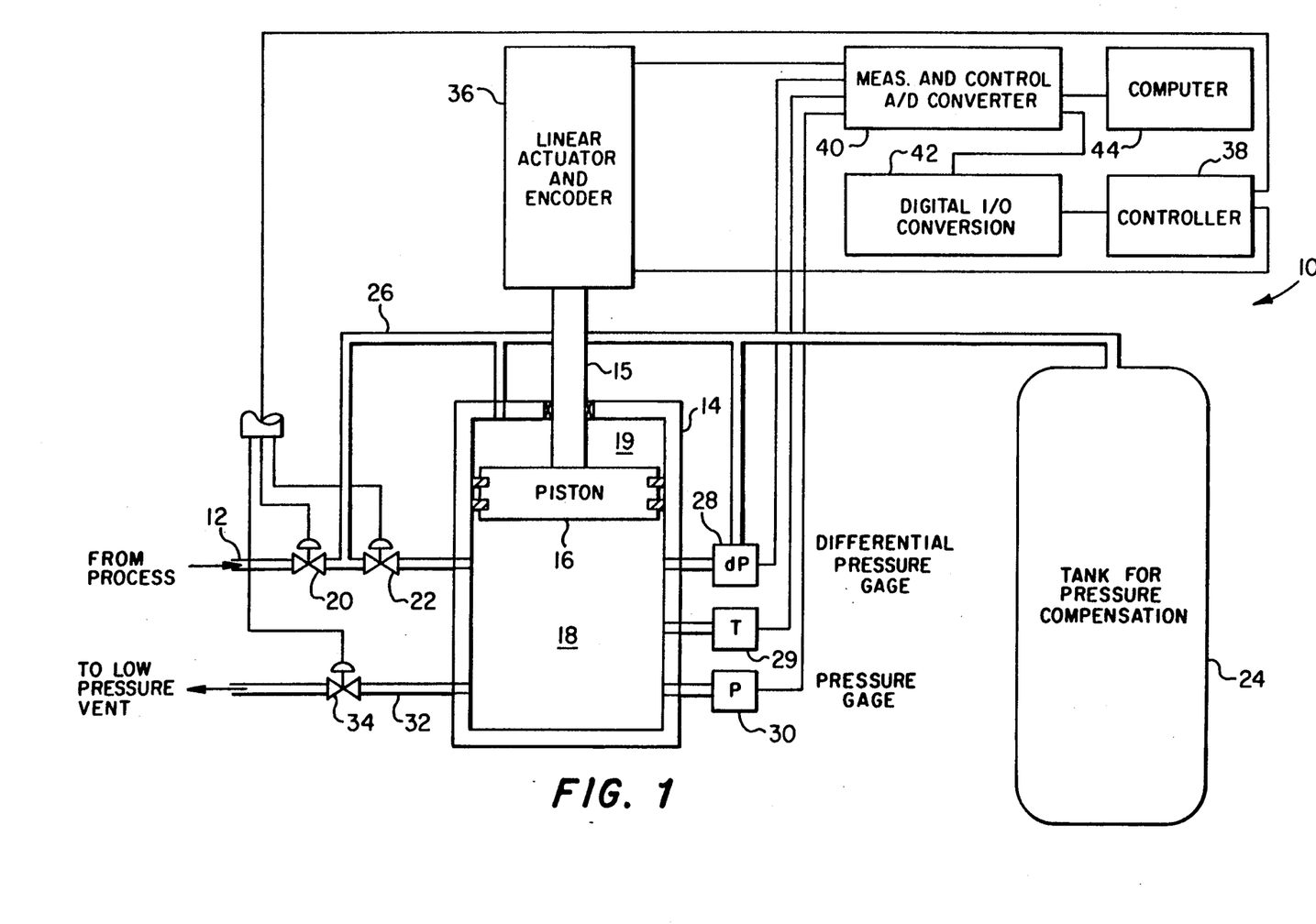
FIG. 1 is a schematic diagram of a system for determining the isentropic exponent of compression of a gas.

Referring to FIG. 1, there is illustrated a system for determining the exponent of compression of a process gas, for example, and generally designated by the numeral 10. The system 10 is adapted to take a gas sample from a process stream, such as a pipeline, not shown, by way of a conduit 12 which is connected to expansible chamber means formed by a cylinder 14 having a reciprocable piston 16 disposed therein and forming an expansible chamber 18. The conduit 12 has two remotely controllable valves 20 and 22 interposed therein. The conduit 12 is also connected to a gas storage tank 24 by way of a branch conduit 26 which is connected to the conduit 12 between the valves 20 and 22. The conduit 26 is also connected to the cylinder 14 for admitting gas to a pressure compensation chamber 19 within the cylinder 14. The conduit 26 is also connected to a differential pressure gauge 28. A temperature gauge 29 may be included in the system 10 to measure the absolute temperature in chamber 18. A pressure gauge 30 is adapted to measure the absolute gas pressure in the chamber 18 and the differential pressure gauge 28 is also adapted to measure the pressure in the chamber 18 and compare that pressure with the pressure in the conduit 26 and 12 which corresponds to the initial pressure in the chamber 18 prior to a compression process. Gas may be vented from the chamber 18 by way of a vent conduit 32 having a remotely controllable shut-off valve 34 interposed therein.

The piston 16 is movable within the cylinder 14 to vary the volume of chamber 18 by a suitable linear actuator and encoder 36 which is operably connected to a controller 38 and a measurement and control analog to digital (A/D) converter 40. The converter 40 and the controller 38 are interconnected by a digital input/output conversion circuit 42. The system 10 also includes a computer or CPU 44 which is adapted to read the position of the piston 16 in the cylinder 14 and the values of pressure and temperature sensed by the gauges 28, 29 and 30 after suitable signal conversion is accomplished by the converter 40. The computer 44 is operable to effect operation of the linear actuator and encoder 36 and the valves 20, 22 and 34 through the circuits 40, 42 and 38, as indicated schematically in FIG. 1.

Figure 2:
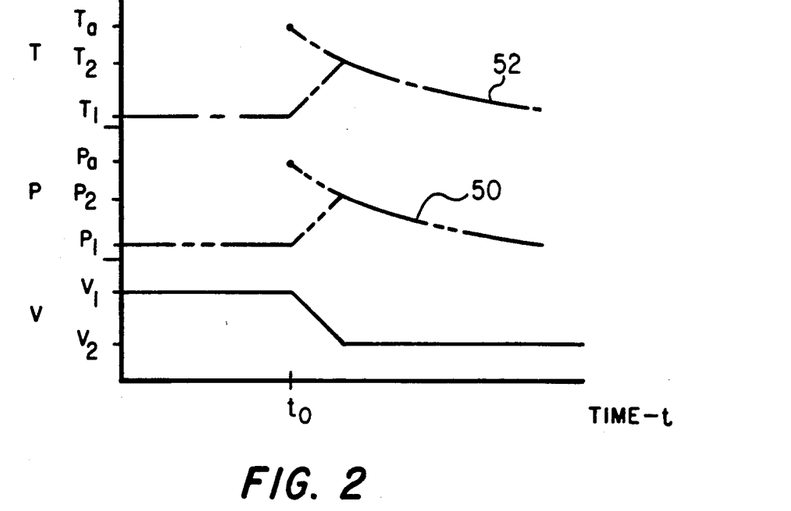
FIG. 2 is a diagram showing the relationship of temperature, pressure and volume versus time during compression of a gas sample with the system of FIG. 1.

The operation of the system 10 to determine the isentropic exponent of compression, k, for an adiabatic process may be carried out generally as described herein and with reference to both FIG. 1 and FIG. 2. The computer 44 may be programmed to carry out all of the operations and calculations necessary for the process to be described. Prior to initiating a sampling of the process gas for measurement and calculation of the exponent, k, the piston 16 would be stroked to purge chamber 18 and returned to the position shown. The valve 34 would be open to vent the chamber 18. Upon initiation of a measurement cycle, the valve 34 is closed and the valves 20 and 22 are opened to admit a sample of process gas to the chamber 18. The valve 22 is then closed and the conditions in chamber 18 are measured, those being the volume of the chamber 18 is $V_1$, the pressure in the chamber 18 is $P_1$ and the temperature in the chamber 18 is $T_1$. The piston 16 is then stroked by the actuator 36 to reduce the volume of chamber 18 to volume $V_2$ over a finite period of time beginning with time $t_0$.

Upon reduction of the volume of the chamber 18 to $V_2$ the pressure is increased to $P_2$, see FIG. 2, and the temperature is raised to $T_2$. A true adiabatic process is not likely due to heat transfer from the gas in the chamber 18 to the cylinder 14 and the piston 16. However, after the piston has been stroked to reduce the volume of chamber 18 to $V_2$, the change in pressure P is measured over a period of time, say at 0.01, 0.02, 0.03 . . . seconds after the start of compression, for example. As the sample of process gas cools in the chamber 18, at the reduced volume, $V_2$, successively recorded pressure values will decrease, and a pressure-versus-time curve 50, FIG. 2, is developed. This curve can be extrapolated back to time zero, ($t_0$), to obtain the pressure based on actual adiabatic compression. This is pressure $P_a$ indicated in FIG. 2. The actual adiabatic temperature rise may also be extrapolated from the curve 52 to yield a value of $T_a$. The curve 52 may also be developed by making temperature measurements at the intervals mentioned above for the pressure measurements. The extrapolation of the curves 50 and 52 may be carried out using conventional curve-fitting techniques. The value of the compression exponent k may then be calculated from the equation:

$$k = [dP/P]/[dV/V] \quad \text{(a)}$$

where dP is the adiabatic pressure increase due to compression as determined from extrapolating the curve 50, dV is the change in volume ($V_1 - V_2$), $P_1$ is the absolute pressure prior to compression and $V_1$ is the volume of chamber 18 prior to compression.

Measurement of differential pressure with the differential pressure gauge 28 is preferred because of the possibilities of relatively high values of absolute pressure of the process gas and the relatively small change in pressure which is obtained in the measurement process. By using the differential pressure gauge 28 for measuring the change in pressure, greater accuracy is obtainable. A one percent (1%) accuracy in determining the compression exponent, k, will result in approximately comparable accuracy in determining the adiabatic efficiency of a compressor. This can be achieved if at least one half of one percent (0.5%) accuracies are obtained in measuring each of dP, dV, $P_1$ and $V_1$. Such accuracies are easily achievable with commercially available measurement devices.

Figure 4:
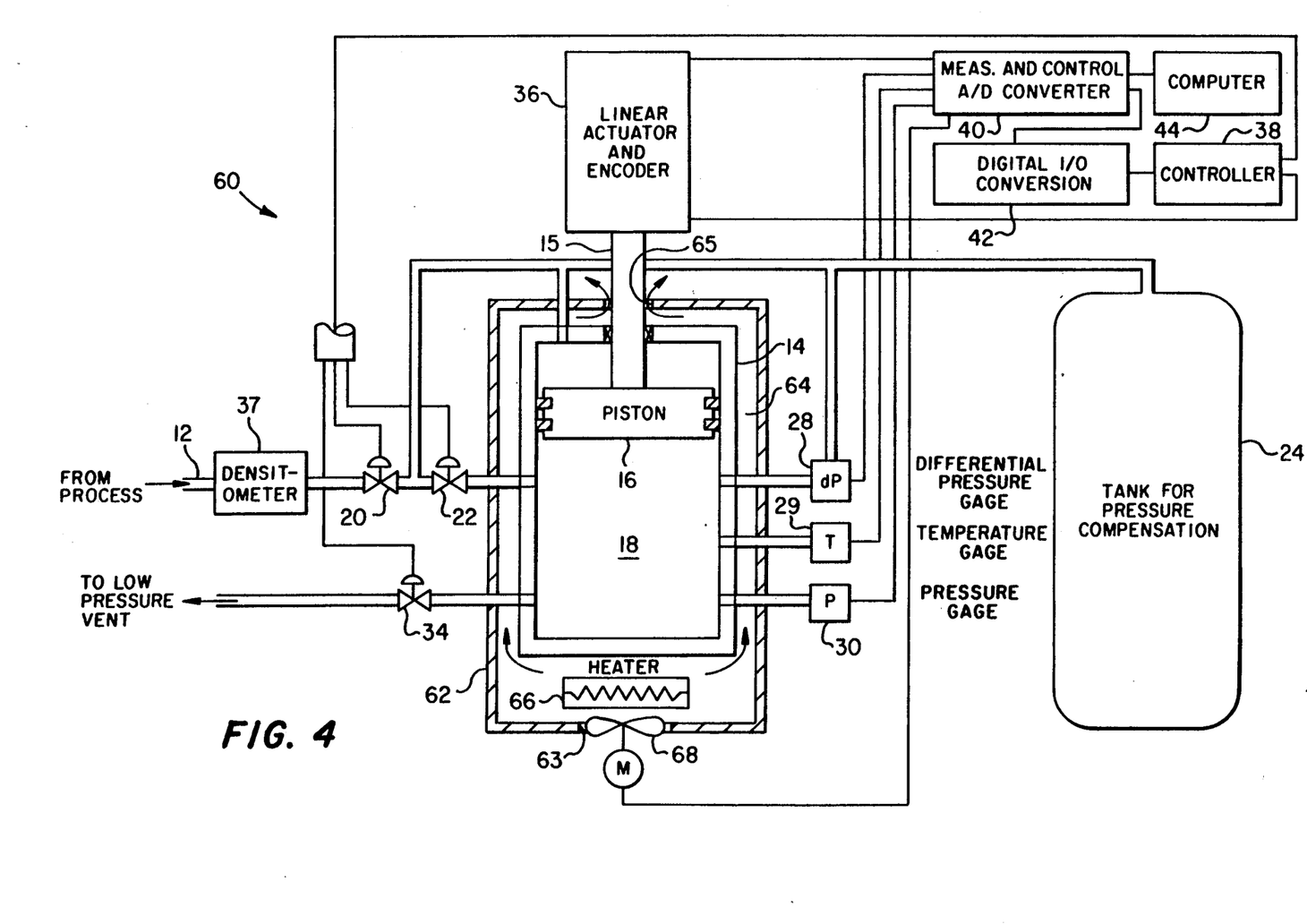
FIG. 4 is a schematic diagram of a system for determining the compressibility factor of a gas sample.

Referring now to FIG. 4, there is illustrated a modified system 60 for measuring the gas compressibility factor, Z. The system 60 includes essentially all of the components of the system 10 with the addition of a shroud 62 disposed around the cylinder 14 and providing a flow path for fluid (air, for example) to flow through the space 64 between the shroud and the cylinder 14 at a controlled temperature as controlled by a suitable heater or heat exchanger 66 through which ambient air may be blown by a motor-driven fan 68. Heat exchange air is admitted to the space 64 through an opening 63 and may exit through a second opening 65 disposed around the actuating shaft 15 interconnecting the actuator 36 with the piston 16. The system 60 also includes a densitometer 37 interposed in conduit 12 for measuring the density of the gas sample. The densitometer 37 may be one of the SL series gas densitometers made by EG&G Chandler Engineering, Tulsa, Okla. Accordingly, as will be further appreciated herein, gas molecular weight may also be determined after determining the compressibility factor.

A process for determining the compressibility factor Z will now be described, referring, in part, to FIG. 4. After purging chamber 18 a sample of process gas is admitted into the chamber after closure of valve 34 and opening of valves 20 and 22. Valve 22 is then closed. The controller 38 then operates the motor-driven fan 68 and the heat exchanger 66 to bring the sample of gas in the chamber 18 to a predetermined temperature value, $T_1$. The pressure of the gas sample in the chamber 18, $P_1$, and the temperature $T_1$ as well as the volume $V_1$ are then measured and recorded. The volume of chamber 18 is then reduced to $V_2$ to compress the gas sample therein by actuation of the piston 16 with the computer-controlled actuator and encoder 36. The motor-driven fan 68 and the heat exchanger 66 are then operated in a manner to bring the temperature of the gas sample in the chamber 18 to the same temperature previously determined, that is $T_2$ is made equal to $T_1$. The pressure $P_2$, and the Volume $V_2$ are also then measured and recorded. Finally, the motor-driven fan 68 and the heat exchanger 66 are operated to raise the temperature of the gas sample in the chamber 18 by a predetermined amount, say about 50° F., to temperature $T_3$ and the pressure $P_3$, the temperature $T_3$ are recorded. The volume remains unchanged so that $V_3$ equals $V_2$. The values of pressure, temperature and volume at condition "3" are then also measured and recorded.

The compressibility factor Z, together with temperature, pressure and volume ratios are then computed and values of the compressibility factor are obtained in accordance with the following procedure.

The quantities of pressure, temperature and volume ratio $P_R$, $T_R$ and $V_R$ may be used herein to designate various conditions. For example:

$$T_2 = T_1 \text{ and} \quad (1)$$

$$V_3 = V_2 \quad (2)$$

$$P_{R21} = P_2/P_1$$

$$T_{R21} = T_2/T_1 = 1$$

$$V_{R21} = V_2/V_1$$

The compressibility factor Z for each condition may be expressed as follows:

$$Z_2/Z_1 = (P_2/P_1) \cdot (V_2/V_1) \quad (3)$$

$$P_{R32} = P_3/P_2$$

$$T_{R32} = T_3/T_2$$

$$V_{R32} V_3/V_2 = 1$$

$$Z_3/Z_2 = (P_3/P_2) \cdot (T_2/T_3) \quad (4)$$

Equations (3) and (4) are based on the "non-ideal" gas law wherein:

$$\text{density} = W/V = MP/10.73(TZ) \quad (b)$$

$$\therefore PV/TZ = W10.73/M = \text{constant}$$

where:
  W = pounds of gas
  V = volume of gas
  M = gas molecular weight
  P,T = pressure, temperature
  Z = compressibility factor Thus, when a sample of gas has its P, V and T changed from conditions "1" to "2" to "3" as indicated above:

$$PV/TZ = \text{constant} = P_1 V_1/T_1 Z_1 = P_2 V_2/T_2 Z_2$$

$$\therefore Z_2/Z_1 = (P_2/P_1)(V_2/V_1) \text{ for the condition where } T_1 = T_2,$$

and analogously for the change from $(P_2, V_2, T_2)$ to $(P_3, V_3, T_3)$ $Z_3/Z_2 = (P_3/P_2)(T_2/T_3)$ for the condition where $V_3 = V_2$.

$Z_2/Z_1$ and $Z_3/Z_2$ are known (from measurements of $P_1, P_2, P_3, V_1, V_2, V_3, T_2, T_3$) and are used in backsolving for pseudo reduced temperature, Tr, and a combination of factors represented by "x" in equations (6) thru (13) below.

A numerical technique utilizing these ratios and the so called Standing-Katz diagram is then carried out to compute a unique value of $Z_2$, as well as the pseudo-critical temperature and pressure $T_{pc}$, $P_{pc}$, of the gas mixture being measured.

Figure 3:
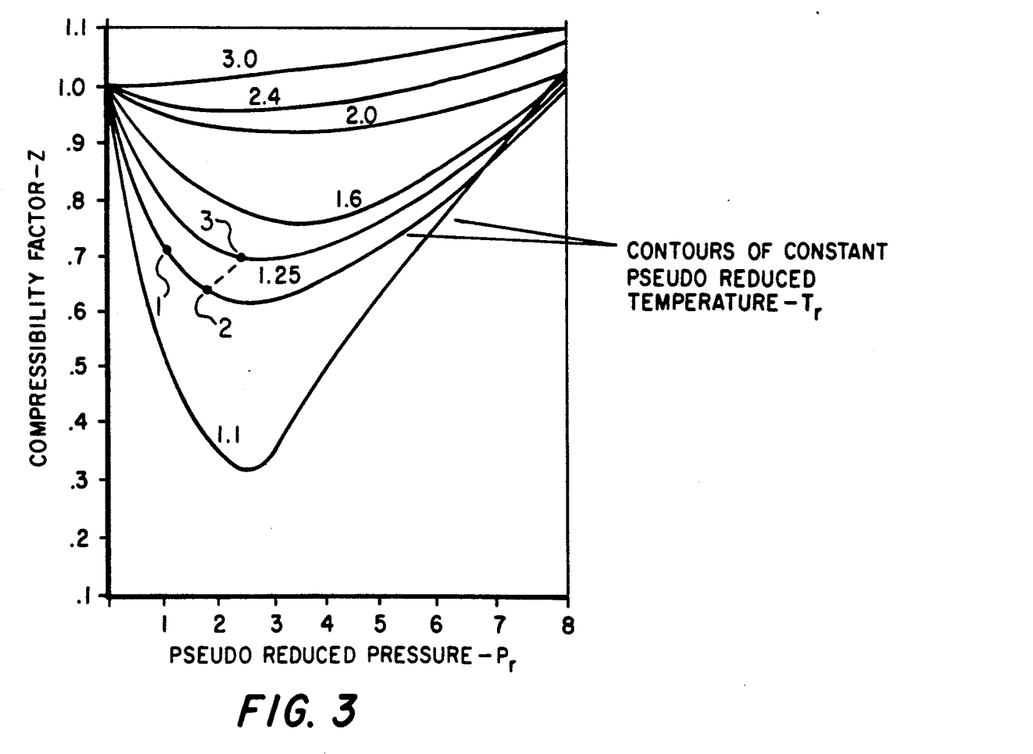
FIG. 3 is a diagram showing the compressibility factor as a function of the pseudo-reduced pressure and pseudo-reduced temperature for a gas.

FIG. 3 is an abbreviated Standing-Katz diagram illustrating its use in solving for the compressibility factor according to the present invention. Further discussion of and a complete showing of Standing-Katz diagrams is described in *Engineering Data Book*, Ninth Ed., Gas Processors Suppliers Association, Tulsa, Okla. FIG. 3 is valid for most gas compositions.

The correlation between the portion of the process of compressing and heating the gas sample and the determination of Z from the measured (P,V,T) data can be carried out as follows:

$(P_1,V_1,T_1),(P_2,V_2,T_2)$ and $(P_3,V_3,T_3)$ are represented by points marked 1,2,3, respectively, in FIG. 3.

The step previously described of compressing the sample and then cooling the sample to make temperature $T_2 = T_1$ results in moving along an isotherm (along pseudo-reduced temperature contour 1.25) because temperature of the sample is restored to $T_1$ via the fan 68.

The step of then raising the temperature of the sample from $T_2$ to $T_3$ results in moving to point 3 in FIG. 3 across isotherms because the temperature is raised, and across isobars (the pseudo reduced pressure, $P_r$, changes) because the pressure of the gas sample rises when it is heated, but volume is kept constant.

The computational procedure is based on the premise that a unique set of points (1,2,3) can be found which corresponds to the observed (measured) values (ratios of Z)

$$Z_2/Z_1 = (P_2/P_1)(V_2/V_1)$$

$$Z_3/Z_2 = (P_3/P_2)(T_2/T_3)$$

The method further utilizes a curve-fitted form of the curves of the Standing-Katz diagram and a Benedict-Webb-Rubin type equation of state fitted by an eight coefficient form developed by Dranchuk, Purvis and Robinson (1974) both of which are described in *Natural Gas Engineering*, Pennwell Publishing Co., 1980.

Z is a function "f" of only $T_r$ and x:

$$\begin{aligned} Z &= f(T_r, x) \\ &= 1 + B_1 \ast x + B_2 \ast x^2 + B_3 \ast x^5 + \\ &\quad B_4 \ast x^2 \ast (1 + A_8 \ast x^2) \ast \exp(-A_8 \ast x^2) \end{aligned} \quad (5)$$

where,
  $x = 0.27 \ast P_r/(Z \ast T_r)$
  $P_r$ = pseudo-reduced pressure = $P/P_{pc}$
  $P_{pc}$ = pseudo critical pressure
  $T_r$ = pseudo-reduced temperature = $T/T_{pc}$
  $T_{pc}$ = pseudo critical temperature
  $B_1 = A_1 + A_2/T_r + A_3/T_r^3$
  $B_2 = A_4 + A_5/T_r$
  $B_3 = A_5 \ast A_6/T_r$
  $B_4 = A_7/T_r^3$
  $\exp = e = 2.718$ The values of $A_1$ through $A_8$ were derived by Dranchuk, Pervis and Robinson and are as follows:

$A_1 = 0.31506237$
  $A_2 = -1.04670990$
  $A_3 = -0.57832729$
  $A_4 = 0.53530771$
  $A_5 = -0.61232032$
  $A_6 = -0.10488813$
  $A_7 = 0.68157001$
  $A_8 = 0.68446549$

Equation (5) is used to solve for a series of $(T_r, x)$ pairs which satisfy $$Z_2 Z_1 32\ Z_{R21} = f(T_{r2}, x_2)/f(T_{r1}, x_1) \quad (6)$$

and another series which satisfy $$Z_3/Z_2 = Z_{R32} = f(T_{r3}, x_2) \quad (7)$$

where $$T_{r2} = T_2/T_{pc} \quad (8)$$

$$x_2 = 0.27 \ast (P_2/P_{pc})/(Z_2 \ast T_2/T_{pc}) \quad (9)$$

$$T_{r1} = T_1/T_{pc} = T_2/T_{pc} = T_{r2} \quad (10)$$

$$\begin{aligned} x_1 &= 0.27 \ast (P_1/P_{pc})/(Z_1 \ast T_1/T_{pc}) \\ &= x_2 \ast (P_1/P_2) \ast (Z_2/Z_1) = x_2 \ast Z_{R21}/P_{R21} \end{aligned} \quad (11)$$

$$T_{r3} = T_3/T_{pc} = (T_3)/(T_2) T_{r2} \quad (12)$$

-continued $$x_3 = 0.27^*(P_3/P_{pc})/(Z_3^*T_3/T_{pc}) \quad (13)$$
$$= x_2^*(P_3/P_2)^*(Z_2/Z_3)^*(T_2/T_3) = x_2^*P_{R32}/(Z_{R32}^*T_{R32})$$
$$= x_2 \text{ (because } V_{R32} = 1 = Z_{R32}^* T_{R32}/P_{R32})$$

Substituting equations 5 and 8 through 13 in equations 3 and 4 yields that $(T_r,x)$ must satisfy both equations 14 and 15 which are:

$$(P_2/P_1)(V_2/V_1) = f(T_{r2},x_2)/f(T_{r2},(V_2/V_1)x_2) \quad (14)$$

and $$(P_3 P_2)(T_2/T_3) = f((T_3/T_2)T_{r2},x_2)/f(T_{r2},x_2) \quad (15)$$

The $(T_4,x)$ solution pair common to both equations 14 and 15 is then substituted in equation 5 to solve for $Z_2$. Equations 8 and 9 then yield values of $T_{pc}$ and $P_{pc}$.

The solution "pair" of values of pseudo reduced temperature, $T_r$, and parameter "x" may be found using iteration. Predetermined, reasonable ranges of values may be selected such as are indicated in the following example. The calculations may, of course, be carried out by the computer 44.

EXAMPLE

A sample of a gas whose exact composition is unknown is processed by the system 60 with the following conditions and carrying out the measurement steps previously described.

$$T_1 = T_2 = 100°F. = 560°A$$
$$P_2 = 300 \text{ psia}$$

$$\left.\begin{array}{l} P_2/P_1 = 1.1 \\ V_2/V_1 = 0.9 \end{array}\right\} \rightarrow Z_2/Z_1 = 0.99$$

$$\left.\begin{array}{l} P_3/P_2 = 1.155 \\ T_3/T_2 = 1.05 \end{array}\right\} \rightarrow Z_3/Z_2 = 1.05$$

Trial values of $T_r$ between 1.2 and 2.2, for example, are selected and corresponding values of constant $B_1$ through $B_4$ are determined using the given values of $A_1$ through $A_8$. Trial values of the x parameter of between 0.10 and 1.0 are selected to give trial values of $Z_2$, computed by equation (5).

For the same set of trial values of $T_r$ corresponding values of $Z_1$ are obtained by multiplying the trial values of x by $V_2/V_1$. Accordingly, a table of values of $Z_2/Z_1$ is obtainable for the trial values of x.

Figure 5:
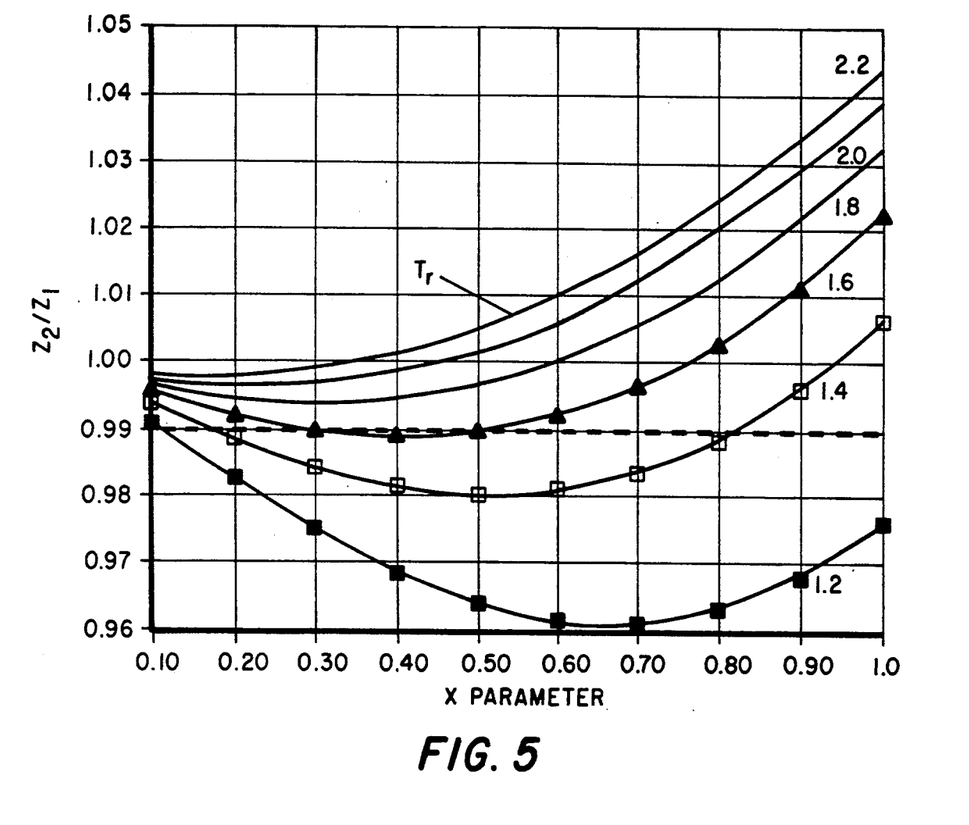
FIGS. 5 through 7 are diagrams illustrating values of certain parameters used in the method of the present invention.

A plot of the values of x, $Z_2/Z_1$ and $T_r$ is shown in FIG. 5. Value pairs of $T_r$ and x corresponding to $Z_2/Z_1 = 0.99$ are obtainable from FIG. 5, by way of example.

Figure 6:
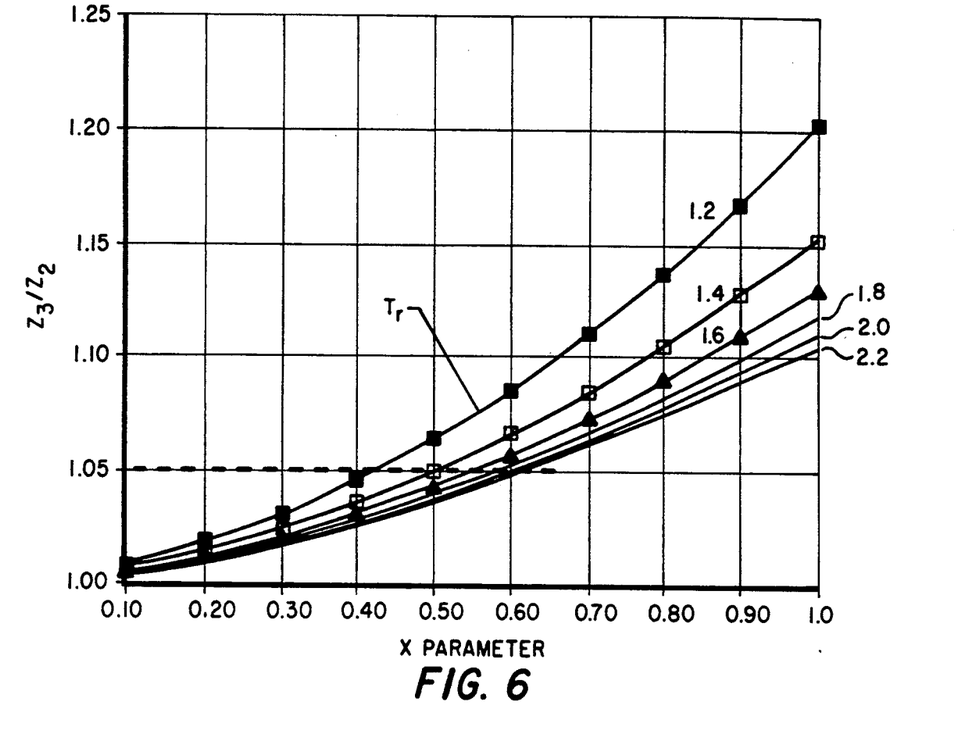

In like manner values of $T_r$ and x corresponding to $Z_3/Z_2 = 1.05$ may be obtained using the same calculation procedure. The values of Tr are modified by the relationship $T_r^*(T_3/T_2)$. FIG. 6 illustrates values of $T_r$ and x corresponding to $Z_3/Z_2 = 1.05$.

Figure 7:
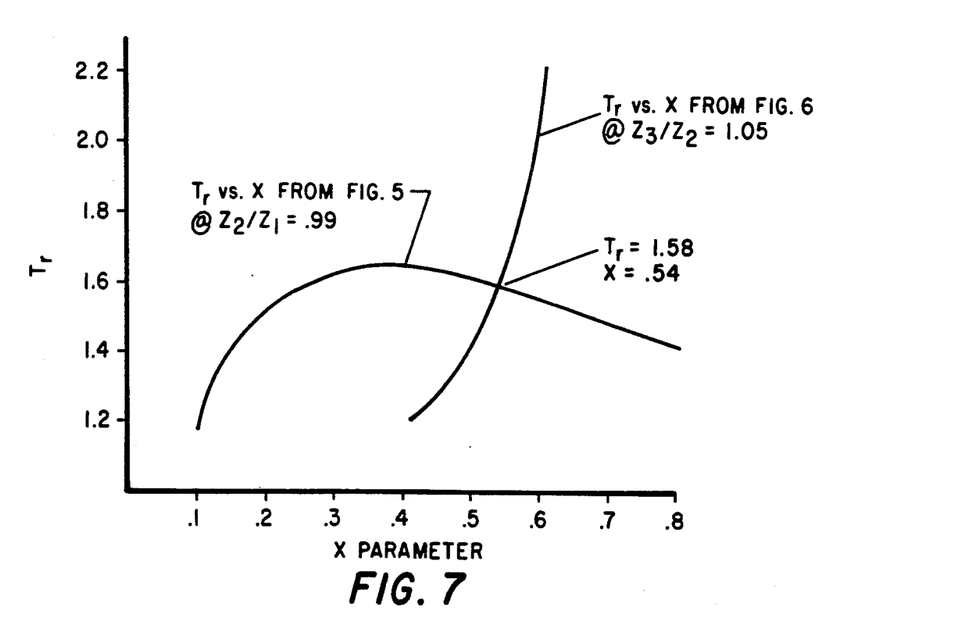

The values of $T_r$ and x that satisfy both relationships of $Z_2/Z_1$ and $Z_3/Z_2$ may be obtained by the plots of the values of $T_r$ and x that are derived from FIGS. 5 and 6 corresponding to the predetermined values of the ratio of the compressibility factor. FIG. 7 shows the values of $T_r$ and x that are such a solution.

The compressibility factor Z, and pseudo critical pressure and temperature ($P_{pc}$, $T_{pc}$) are then computed using equations (5), (9) and (8), respectively.

Molecular weight of the gas in question may also be calculated from a measured value of density and the calculated value of the compressibility factor, Z, using equation (b).

An alternate embodiment of the technique just described for determining the compressibility factor, Z, may be carried out using the apparatus illustrated in FIG. 4 wherein successive compression processes are carried out from condition 1 to condition 2 to condition 3. After the first compression step from condition 1 to condition 2, the temperature of the gas in the chamber 18 is returned to the value $T_1$. In other words, $T_2 = T_1$. After the pressure and volume values are measured at condition 2, the chamber 18 is further reduced in volume to condition 3 and the temperature of the gas is again returned from whatever value it reaches to the value of temperature, $T_1$. Accordingly, $$T_1 = T_2 = T_3 \quad (16)$$

The "non-ideal" gas law (equation "b") then yields $$\frac{Z_2}{Z_1} = \frac{P_2 V_2}{P_1 V_1} \quad (17)$$

$$\frac{Z_3}{Z_2} = \frac{P_3 V_3}{P_2 V_2} \quad (18)$$

$Z_2 Z_1$ and $Z_3/Z_2$ are evaluated using measured values of ($P_1$, $P_2$, $P_3$, $V_1$, $V_2$, $V_3$).

The solution for $Z_2$, MW, $P_{pc}$, $T_{pc}$ is obtained in the same way as already described in the first embodiment, with the exception that the ratio $Z_3 Z_2$ is calculated via equation 18 instead of 4.

That is, equation (5) is used to solve for a series of $(T_r,x)$ pairs which satisfy $$Z_2/Z_1 = Z_{R21} = f(T_{r2},x_2)/f(T_{r1},x_1) \quad (19)$$

and another series which satisfy $$Z_3/Z_2 = Z_{R32} = f(T_{r3},x_3)/f(T_{r2},x_2) \quad (20)$$

where $$T_{r2} = T_2/T_{pc} \quad (21)$$

$$x_2 = 0.27^*(P_2/P_{pc})/(Z_2^*T_2/T_{pc}) \quad (22)$$

$$T_{r1} = T_1/T_{pc} = T_2/T_{pc} = T_{r2} \quad (23)$$

$$x_1 = 0.27^*(P_1/P_{pc})/(Z_1^*T_1/T_{pc}) \quad (24)$$
$$= x_2^*(P_1/P_2)^*(Z_2/Z_1) = x_2^*Z_{R21}/P_{R21}/P_{R21} = x_2 V_{R21}$$

$$T_{r3} = T_3/T_{pc} = T_2/T_{pc} = T_{r2} \quad (25)$$

$$x_3 = 0.27^*(P_3/P_{pc})/(Z_3^*T_3/T_{pc}) \quad (26)$$
$$= x_2^*(P_3/P_2)^*(Z_2/Z_3) = (T_2/T_3) = x_2^*P_{R32}/Z_{R32}$$
$$= x_2/V_{R32}$$

Substituting equations 5 and 21 through 26 in equations 17 and 18 yields that $(T_r, x)$ must satisfy both equations 27 and 28 which are:

$$(P_2/P_1)(V_2/V_1) = f(T_{r2}, x_2)/f(T_{r2}, (V_2/V_1)x_2) \quad (27)$$

and $$(P_3/P_2)(V_3/V_2) = f(T_{r2}, (V_2/V_1)x_2)/f(T_{r2}, (V_3/V_2)X_2) \quad (28)$$

The $(T_r, x)$ solution pair common to both equations 27 and 28 is then substituted in equation 5 to solve for $Z_2$. Equations 21 and 22 then yield values of $T_{pc}$ and $P_{pc}$.

Still further, a second alternate embodiment of the method of the present invention for determining the compressibility factor may be carried out using the apparatus of FIG. 4 wherein the volume of the chamber 18 is held constant for three different conditions and the temperature, T, is raised from condition 1 to condition 2 and then to condition 3.

Since volume is kept constant, $$V_1 = V_2 = V_3 \quad (29)$$

The "non-ideal" gas law then yields $$\frac{Z_2}{Z_1} = \frac{P_2 T_1}{P_1 T_2} \quad (30)$$

$$\frac{Z_3}{Z_2} = \frac{P_3 T_2}{P_2 T_3} \quad (31)$$

$Z_2/Z_1$ and $Z_3/Z_2$ are evaluated using measured values of $(P_1, P_2, P_3, T_1, T_2, T_3)$.

The solution for $Z_2$, MW, $P_{pc}$, $T_{pc}$ is obtained in the same way as already described in the first embodiment, with the exception that the ratio $Z_2/Z_1$ is calculated via equation 30 instead of equation 3.

That is, equation (5) is used to solve for a series of $(T_r, x)$ pairs which satisfy $$Z_2/Z_1 = Z_{R21} = f(T_{r2}, x_2)/f(T_{r1}, x_1) \quad (32)$$

and another series which satisfy $$Z_3/Z_2 = Z_{R32} = f(T_{R3}, x_3)/f(T_{r2}, x_2) \quad (33)$$

where $$T_{r2} = T_{pc} \quad (34)$$

$$x_2 = 0.27 \cdot (P_2/P_{pc})/(Z_2 \cdot T_2/T_{pc}) \quad (35)$$

$$T_{r1} = T_1/T_{pc} = (T_1/T_2)T_{r2} = T_{r2}T_{R21} \quad (36)$$

$$\begin{aligned} x_1 &= 0.27 \cdot (P_1/P_{pc})/(Z_1 \cdot T_1/T_{pc}) \\ &= x_2 \cdot (P_1/P_2)(Z_2/Z_1)(T_2/T_1) = x_2 V_{R21} = x_2 \end{aligned} \quad (37)$$

$$T_{r3} = T_3/T_{pc} = (T_3)/(T_2)T_{r2} = T_{r2}T_{R32} \quad (38)$$

$$\begin{aligned} x_3 &= 0.27 \cdot (P_3/P_{pc})/(Z_3 \cdot T_3/T_{pc}) \\ &= x_2 \cdot (P_2/P_3) \cdot (Z_3/Z_2)(T_3/T_2) = x_2 V_{R32} = x_2 \end{aligned} \quad (9)$$

Substituting equations 5 and 34 through 39 in equations 30 and 31 yields that $(T_r, x)$ must satisfy both equations 40 and 41 which are:

$$(P_2/P_1)(T_1/T_2) = f(T_{r2}, x_2)/f((T_1/T_2)T_{r2}, x_2) \quad (40)$$

and $$(P_3/P_2)(T_2/T_3) = f((T_3/T_2)T_{r2}, x_2)/f(T_{r2}, x_2) \quad (41)$$

The $(T_r, x)$ solution pair common to both equations 40 and 41 is then substituted in equation 5 to solve for $Z_2$. Equations 34 and 35 then yield values of $T_{pc}$ and $P_{pc}$.

Although preferred embodiments of systems and methods in accordance with the present invention have been described in detail hereinabove, those skilled in the art will recognize that various substitutions and modifications may be made to the embodiments described without departing from the scope and spirit of the invention as recited in the appended claims.

What is claimed is:

1. A method for determining the compression exponent of a gas process stream comprising the steps of:
    providing means for taking a gas sample from said process stream comprising means forming an expansible chamber, means for changing the volume of said expansible chamber, means for measuring the gas temperature and pressure in said expansible chamber as a function of time and means for measuring said change in volume of said expansible chamber as a function of time;
    admitting a sample of said gas to said expansible chamber and reducing the volume of said expansible chamber to increase the pressure of the gas sample in said expansible chamber;
    measuring the increased pressure in said expansible chamber at the completion of said change in volume;
    measuring the change in pressure as a function of time after completion of said change in volume of said expansible chamber; and
    determining the increase in pressure which would result from an instantaneous change in volume based on extrapolation of a curve of said change in pressure as a function of time.

2. The method set forth in claim 1 wherein:
    said compression is carried out without adding heat to said gas sample.

3. The method set forth in claim 1 wherein:
    the method is carried out to determine the isentropic compression exponent, k, from the equation:

$$k = [dP/P]/[dV/V]$$

where dP is the adiabatic pressure increase due to compression as determined from extrapolating said curve, dV is the change in volume in said chamber and P and V are the initial pressure and volume of said gas sample, respectively.

4. The method set forth in claim 1 wherein:
    said means for measuring includes a differential pressure gauge for measuring the differential pressure between the process stream and the expansible chamber.

5. A system for measuring the compression exponent of a gas comprising:
    means forming an expansible chamber for receiving a sample of said gas and for compressing said gas sample from a first volume to a second volume;
    actuator means for reducing the volume of said expansible chamber from said first volume to said second volume;

temperature measurement means for measuring the temperature in said expansible chamber;

pressure measurement means for measuring the change in pressure in said expansible chamber as a result of said compression; and control means for admitting a sample of gas to said expansible chamber, compressing said sample of gas in said expansible chamber by operation of said actuator means, and measuring the change in temperature and the change in pressure in said chamber as a function of time beginning with the start of compression in said sample in said chamber.

6. A method for determining the compressibility factor, Z, for a sample of a gas composition comprising the steps of:

providing means forming an expansible chamber for compressing a sample of the gas composition from a first volume to a second volume, including means for changing the temperature of the gas sample in said chamber;

admitting a sample of gas to said chamber and measuring the pressure, volume, and temperature of said gas sample at a first condition;

compressing said gas sample to reduce the volume of said chamber to a second condition;

changing the temperature of said gas sample at said second condition to the temperature of said gas sample at said first condition and measuring the pressure and volume of said gas sample in said chamber at said second condition;

changing the temperature of said gas sample in said chamber to a third condition and measuring the pressure, temperature and volume of said gas sample in said chamber at said third condition;

calculating the ratio of the compressibility factor at said second condition to said first condition based on the ratios of pressure and volume at said second condition and said first condition, respectively;

calculating the ratio of the compressibility factor at said third condition to said second condition based on the ratios of the pressures and temperatures at said third condition and said second condition, respectively; and comparing the values of the ratios of compressibility factors to determine the compressibility factor at one of said first, second and third conditions.

7. The method set forth in claim 6 wherein:

the step of comparing the values of the ratios of compressibility factors includes determining a pseudo-reduced temperature value and the value of a parameter which satisfies a curve fitted form of a Standing Katz curve which is common to both ratios of compressibility factor to determine the compressibility factor of said gas sample.

8. The method set forth in claim 7 including the steps of:

selecting trial values of the pseudo-reduced temperature and the parameter to find the values of each which satisfy said curve fitted form.

9. The method set forth in claim 6 including the steps of:

determining the molecular weight of said gas sample by measuring the density of said gas sample and calculating the molecular weight of said gas sample based on said density, the value of the compressibility factor, and the pressure and temperature of said gas sample at one of said conditions.

10. A method for determining the compressibility factor, Z, for a sample of a gas composition comprising the steps of:

providing means forming an expansible chamber for compressing a sample of the gas composition from a first volume to a second volume and a third volume, said chamber including means for changing the temperature of the gas sample in said chamber;

admitting a sample of gas to said chamber and measuring the pressure, volume, and temperature of said gas sample at a first condition;

compressing said gas sample to reduce the volume of said chamber to a second condition;

changing the temperature of said gas sample at said second condition to the temperature of said gas sample at said first condition and measuring the pressure and volume of said gas sample in said chamber at said second condition;

compressing said gas sample to reduce the volume of said chamber to a third condition;

changing the temperature of said gas sample in said chamber to said temperature at said first condition and measuring the pressure and volume of said gas sample in said chamber at said third condition;

calculating the ratio of the compressibility factor at said second condition to said first condition based on the ratios of pressure and volume at said second condition and said first condition, respectively;

calculating the ratio of the compressibility factor at said third condition to said second condition based on the ratios of the pressures and volumes at said third condition and said second condition, respectively; and comparing the values of the ratios of compressibility factors to determine the compressibility factor at one of said first, second and third conditions.

11. The method set forth in claim 10 wherein:

the step of comparing the values of the ratios of compressibility factors includes determining a pseudo-reduced temperature value and the value of a parameter which satisfies a curve fitted form of a Standing Katz curve which is common to both ratios of compressibility factor to determine the compressibility factor of said gas sample.

12. The method set forth in claim 11 including the steps of:

selecting trial values of the pseudo-reduced temperature and the parameter to find the values of each which satisfy said curve fitted form.

13. The method set forth in claim 10 including the steps of:

determining the molecular weight of said gas sample by measuring the density of said gas sample and calculating the molecular weight of said gas sample based on said density, the value of the compressibility factor, and the pressure and temperature of said gas sample at one of said conditions.

14. A method for determining the compressibility factor, Z, for a sample of a gas composition comprising the steps of:

providing means forming a closed chamber of constant known volume for holding a sample of said gas composition including means for changing the temperature of the gas sample in said chamber;

admitting a sample of gas to said chamber and measuring the pressure and temperature of said gas sample at a first condition;

changing the temperature of said gas sample to a second condition;

measuring the pressure and temperature of said gas sample in said chamber at said second condition;

changing the temperature of said gas sample in said chamber to a third condition and measuring the pressure and temperature of said gas sample in said chamber at said third condition;

calculating the ratio of the compressibility factor at said second condition to said first condition based on the ratios of pressure and temperature at said second condition and said first condition, respectively;

calculating the ratio of the compressibility factor at said third condition to said second condition based on the ratios of the pressures and temperatures at said third condition and said second condition, respectively; and comparing the values of the ratios of compressibility factors to determine the compressibility factor at one of said first, second and third conditions.

15. The method set forth in claim 14 wherein:

the step of comparing the values of the ratios of compressibility factors includes determining a pseudo-reduced temperature value and the value of a parameter which satisfies a curve fitted form of a Standing Katz curve which is common to both ratios of compressibility factor to determine the compressibility factor of said gas sample.

16. The method set forth in claim 15 including the steps of:

selecting trial values of the pseudo-reduced temperature and the parameter to find the values of each which satisfy said curve fitted form.

17. The method set forth in claim 14 including the steps of:

determining the molecular weight of said gas sample by measuring the density of said gas sample and calculating the molecular weight of said gas sample based on said density, the value of the compressibility factor, and the pressure and temperature of said gas sample at one of said conditions.

18. A system for measuring the compressibility factor of a gas sample from a process stream comprising:

means forming an expansible chamber for receiving a sample of said gas and for compressing said gas from a first volume to a second volume;

actuator means for reducing the volume of said chamber from said first volume to said second volume;

temperature measurement means for measuring the temperature in said chamber;

pressure measurement means for measuring the change in pressure in said chamber as a result of said compression;

control means for admitting a sample of gas to said chamber, compressing said sample of gas in said chamber by operation of said actuator means, measuring the temperature and the pressure in said chamber; and means for changing the temperature of said gas sample in said chamber to at least two preselected temperatures.

19. The system set forth in claim 18 including:

densitometer means for measuring the density of said gas sample.

* * * * *